(12) United States Patent
Iino et al.

(10) Patent No.: US 9,763,671 B2
(45) Date of Patent: Sep. 19, 2017

(54) CUFF COVER AND CUFF FOR USING THE SAME

(75) Inventors: Mitsuo Iino, Noda (JP); Yudai Takeshita, Tokyo (JP)

(73) Assignees: Matsuo Iino, Noda-shi, Chiba (JP); TAKETORA CO., LTD., Tokyo (JP)

( * ) Notice: Subject to any disclaimer, the term of this patent is extended or adjusted under 35 U.S.C. 154(b) by 1800 days.

(21) Appl. No.: 11/727,459

(22) Filed: Mar. 27, 2007

(65) Prior Publication Data

US 2008/0027336 A1    Jan. 31, 2008

(30) Foreign Application Priority Data

Jul. 31, 2006    (JP) ................................ 2006-207883

(51) Int. Cl.
*A61B 5/02* (2006.01)
*A61B 17/135* (2006.01)
*A61B 5/022* (2006.01)
*A61B 5/00* (2006.01)

(52) U.S. Cl.
CPC ........ *A61B 17/135* (2013.01); *A61B 5/02233* (2013.01); *A61B 5/411* (2013.01)

(58) Field of Classification Search
CPC .................................................. A61B 5/02233
USPC ................. 600/485, 490–499; 606/201–203; 128/327, 677, 686; 602/13
See application file for complete search history.

(56) References Cited

U.S. PATENT DOCUMENTS

| | | | | | |
|---|---|---|---|---|---|
| 3,699,945 | A | * | 10/1972 | Hanafin | 600/499 |
| 4,716,906 | A | * | 1/1988 | Ruff | 600/499 |
| 5,228,448 | A | * | 7/1993 | Byrd | 600/490 |
| 2001/0016698 | A1 | * | 8/2001 | Lloyd | 602/3 |

* cited by examiner

*Primary Examiner* — Patricia Mallari
*Assistant Examiner* — Vasuda Ramachandran
(74) *Attorney, Agent, or Firm* — Manabu Kanesaka

(57) ABSTRACT

There is provided a throwaway cuff cover capable of being used for all types of cuffs and performing triage at the same time. The cuff cover has a long main cover 20 which is wound around the upper arm of the human body and a sub-cover 30 shorter than the main cover 20, the sub-cover 30 being provided connectingly along one side of the main cover 20 and capable of being folded onto the main cover 20 side, and the cuff housing portions 21 and 31 are allotted to the main cover 20 and the sub-cover 30, respectively.

15 Claims, 5 Drawing Sheets

CUFF COVER AND CUFF FOR USING THE SAME

TECHNICAL FIELD

The present invention relates to a cuff cover attached to a cuff for measuring blood pressure. More particularly, it relates to a throwaway cuff cover that considers the prevention of cuff contamination and the physical burden of patient, and also can perform triage at the same time.

BACKGROUND ART

In the case where an accident or disaster occurs, a large number of injured persons and sick persons may rush to medical facilities for a short period of time in want of medical care. However, the functions (medical staff, equipment, medical supplies, etc.) of medical facilities are limited. In order to provide the largest possible number of sick and injured persons with medical treatment under restricted conditions at the time of disaster, it is necessary to determine the priority order of medical treatment and backward conveyance according to the urgency and seriousness of sickness and injuries.

The work for determining such a priority order is called "triage", and for the triage, an identification tag called a triage tag is used. Usually, the triage tag is color-coded into four stages (red, yellow, green, and black) according to the urgency and seriousness of sickness and injuries, and is used by being attached to the patient's body. The triage tag is also used as a simplified chart describing the symptom, blood pressure, blood type, and the like of a patient.

Usually, for the triage work, a doctor or nurse called a triage officer (a person responsible for execution of triage) makes determination, and at the same time, measures the patient's blood pressure, heart rate, and the like.

Generally, the use of medical appliances for an unspecified large number of patients may cause secondary damage such as blood infection. Therefore, the secondary usage of injection needles and the like is prohibited absolutely. Also, since a cuff used for measuring blood pressure has a large contact area with the patient's body, the cuff having been used once must be sterilized surely.

However, in the case of the above-described emergency, it is difficult to remove a cuff cover one by one from the cuff and to sterilize the cuff cover. Accordingly, a throwaway cuff cover as disclosed, for example, in Patent Document 1 (Japanese Patent Application Publication No. H08-579) has been proposed.

This disclosed cuff cover can cover up the cuff by affixing a sheet made of nonwoven fabric or paper to the cuff. However, this cuff cover has problems as described below.

Generally, manometers include a mercury manometer, aneroid manometer, and automatic manometer, and the shape of cuff differs according to the type of manometer. Therefore, it is impossible to use the cuff cover described in Patent Document 1 for all types of cuffs.

Also, some cuffs are of a large-size type integrating the cover. The proposed cover cannot be affixed to this type of cuff. Furthermore, the affixation of the cuff cover described in Patent Document 1 to the cuff at the emergency time as described above is almost impossible in terms of time and manpower.

SUMMARY OF THE INVENTION

The present invention has been made to solve the above problems, and accordingly an object thereof is to provide a throwaway cuff cover capable of being used for all types of cuffs and performing triage at the same time.

To achieve the above object, the present invention has some features described below. The present invention provides a cuff cover which houses a cuff for measuring blood pressure therein, wherein at least two cuff housing portions used selectively according to the size of the cuff are provided.

According to this configuration, since the cuff housing portions used selectively according to the size of the cuff are provided, one cuff cover can be used for a plurality of types of cuffs.

The present invention is characterized in that the cuff cover has a long main cover which is wound around the upper arm of the human body and a sub-cover shorter than the main cover, the sub-cover being provided connectingly along one side of the main cover and capable of being folded onto the main cover side, and the cuff housing portions are allotted to the main cover and the sub-cover.

According to this configuration, a large cuff for, for example, an aneroid manometer is housed in the cuff housing portion on the main cover side, and a small standard-size cuff for, for example, a mercury manometer is housed in the cuff housing portion on the sub-cover side, so that the cuff housing portions can be used for different purposes according to the size of the cuff.

As a more favorable mode, the main cover is provided with a first tube pull-out hole for pulling out cuff tubes provided on the cuff from the cuff housing portion.

As a more favorable mode, the first tube pull-out hole is provided at least at two places of the main cover.

According to this configuration, since the first tube pull-out hole for pulling out the cuff tubes is provided at two places in the cuff housing portion of the main cover, the pull-out position of the cuff tubes can be changed freely according to the size and shape of the cuff.

As a further favorable mode, the sub-cover is provided with a second tube pull-out hole for pulling out the cuff tubes provided on the cuff from the cuff housing portion.

According to this configuration, since the second tube pull-out hole for pulling out the cuff tubes is provided also in the cuff housing portion of the sub-cover, the cuff tubes can be pulled out easily to the outside of the cover.

Also, the present invention is characterized in that the main cover and the sub-cover are provided with fixing means for fixing the covers to each other in a lapped state.

According to this configuration, since the fixing means for fixing the main cover and the sub-cover to each other in a lapped state is provided, the sub-cover can be fixed to the main cover in a folded state, and the sub-cover can be prevented from being shifted by the pressure of the cuff.

The present invention is characterized in that the main cover is provided with positioning means for aligning the center of the cuff with the upper arm artery when the main cover is wound around the upper arm.

According to this configuration, since the positioning means for aligning the center of the cuff with the upper arm artery when the main cover is wound around the upper arm is provided in a part of the main cover, the cuff can be mounted on the upper arm rapidly and exactly.

The present invention is characterized in that the main cover is provided with a pair of surface fasteners for fixing the main cover in a state of being wound around the upper arm, and on the engagingly attaching surface of the surface fastener, a first alarm means is provided to indicate a shift of the engagingly attaching state in the circumferential direction due to the pressure of the cuff.

According to this configuration, since the first alarm means for indicating a shift in the circumferential direction of the main cover due to the pressure of the cuff is provided in a part of the engagingly attaching surface of the paired surface fasteners provided on the main cover, a positional shift in the circumferential direction of the cuff can be discriminated easily, and hence the correction of position can be made easily.

The present invention is characterized in that the sub-cover is provided with a second alarm means which indicates a shift in the axial direction when the cuff is expanded in a state of being wound around the upper arm.

According to this configuration, since the second alarm means which indicates that a shift in the axial direction is produced by the pressure of the cuff is further provided in a part of the sub-cover, a positional shift in the axial direction of the cuff can be discriminated easily, and hence the correction of position can be made easily.

The present invention provides a cuff cover which houses a cuff for measuring blood pressure therein, wherein a positioning means is provided to align the center of the cuff with the upper arm artery when the cuff cover is wound around the upper arm.

According to this configuration, the center of the cuff can be aligned easily with the position of the upper arm artery.

In a cuff cover which houses a cuff for measuring blood pressure therein, a pair of surface fasteners are provided to fix the cuff cover in a state of being wound around the upper arm, and on the engagingly attaching surface of the surface fastener, a first alarm means is provided to indicate a shift of the engagingly attaching state in the circumferential direction due to the pressure of the cuff.

More favorably, in a cuff cover which houses a cuff for measuring blood pressure therein, a second alarm means is provided to indicate a shift in the axial direction when the cuff is expanded in a state of being wound around the upper arm.

According to these configurations, since the first alarm means and the second alarm means that indicate shifts of the engagingly attaching state in the circumferential and axial directions of the cuff are provided, shifts in the circumferential and axial directions of the cuff due to the pressure of the cuff can be discriminated easily.

In a cuff cover which houses a cuff for measuring blood pressure therein, the cuff cover is provided with a feature describing portion for describing physical conditions and features of a wearer.

In a cuff cover which houses a cuff for measuring blood pressure therein, the cuff cover is color-coded according to triage or the physical conditions, the distinction of sex, and the conditions of injuries of a wearer.

According to the present invention, the cuff cover has the feature describing portion for describing the physical conditions and features of a wearer, and also is color-coded according to the physical conditions and the distinction of sex of a wearer, so that the cuff cover can be used as a triage tag.

The present invention embraces a cuff having the cuff cover described above.

That is to say, by using the cuff mounted with the cuff cover in accordance with the present invention, a series of medical work from conveyance to medical care can be performed while the cuff is attached to one patient, and also the cuff cover can perform a function as a triage tag at the time of emergency.

DETAILED DESCRIPTION

Figure 1:
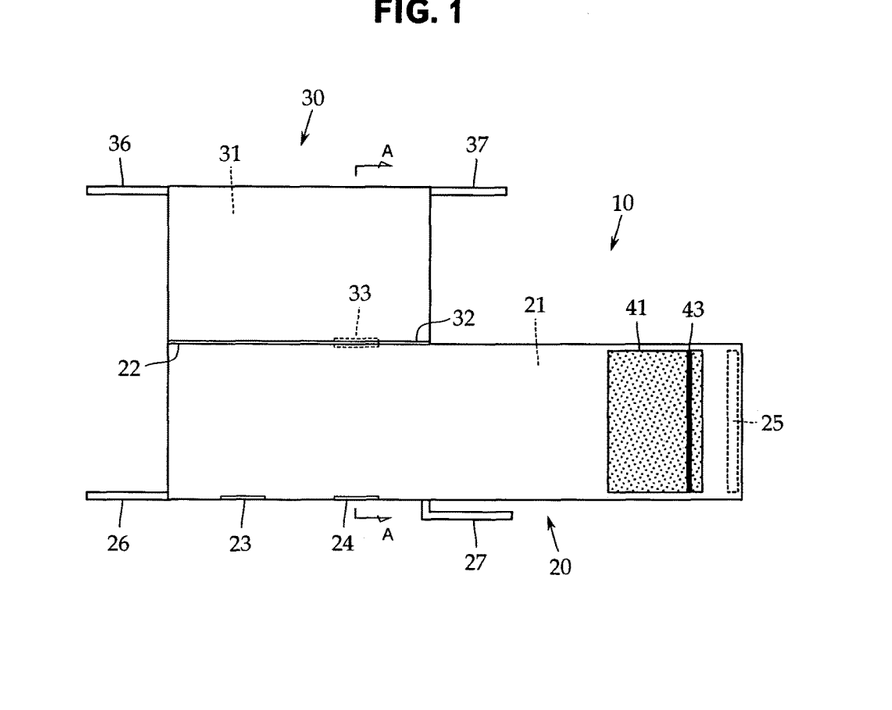
FIG. 1 is a front view of a cuff cover in accordance with one embodiment of the present invention.
Figure 2:
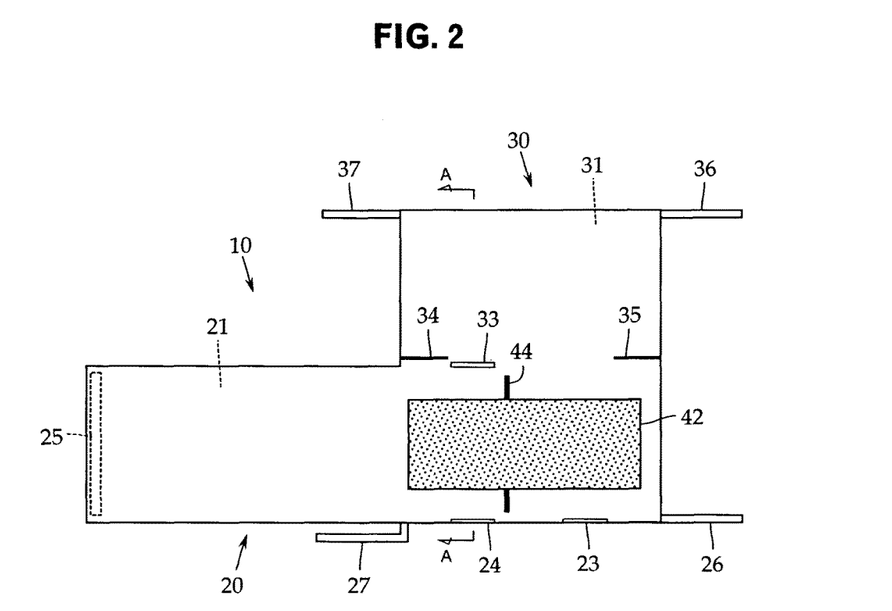
FIG. 2 is a back view of a cuff cover in accordance with one embodiment of the present invention.
Figure 3:
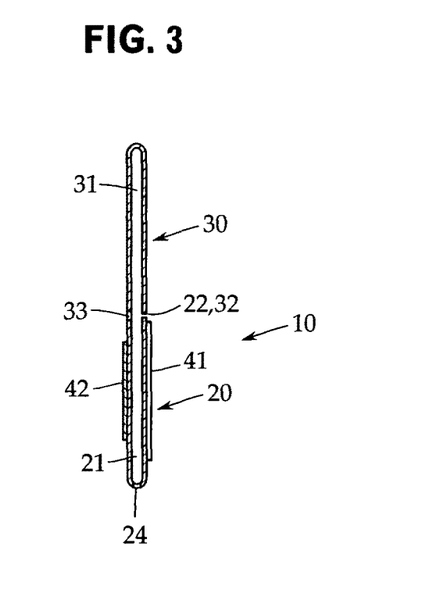
FIG. 3 is a sectional view taken along the line A-A of FIGS. 1 and 2.

A cuff cover in accordance with the present invention will now be described with reference to the accompanying drawings. FIG. 1 is a front view of the cuff cover in accordance with one embodiment of the present invention, FIG. 2 is a back view thereof, and FIG. 3 is a sectional view taken along the line A-A of FIGS. 1 and 2.

As shown in FIG. 1, a cuff cover 10 includes a long main cover 20 that is wound around the upper arm of the human body and a sub-cover 30 shorter than the main cover 20, the sub-cover 30 being connected integrally to one side (the upper side in FIG. 1) of the main cover 20.

The cuff cover 10 is formed by sewing up one nonwoven fabric, and various pieces of information such as the distinction of sex, the blood type, and the symptom of the wearer can be written on the surface of the cuff cover 10 by using an oil-based pen or the like.

In this example, a nonwoven fabric is used for the cuff cover 10. However, the cuff cover 10 may be made of paper or cloth. The material of the cuff cover 10 in accordance with the present invention is not subject to any special restriction if the material is low in cost, has high permeability and strength withstanding the pressure of a cuff, and enables the writing of characters using a pen.

The whole of the top surface of the cuff cover 10 is a feature describing portion enabling the writing using a pen. Also, on the cuff cover 10, a chart form for writing the blood pressure, blood type, age, symptom, allergy, and the like of the wearer may be printed.

The cuff cover 10 is color-coded according to triage or the physical conditions, the distinction of sex, and the conditions of injuries of the wearer. That is to say, the cuff cover 10 can be used also as a triage tag together with the above-described feature describing portion at the time of emergency.

Also, the cuff cover 10 can be used so that the medical staff can judge, at a glance, the individual feature of the patient such that the patient is a carrier of hepatitis virus or is pregnant. Preferable colors are white, green, yellow, red, blue, and pink. However, any color other than the above may be used.

Figure 4:
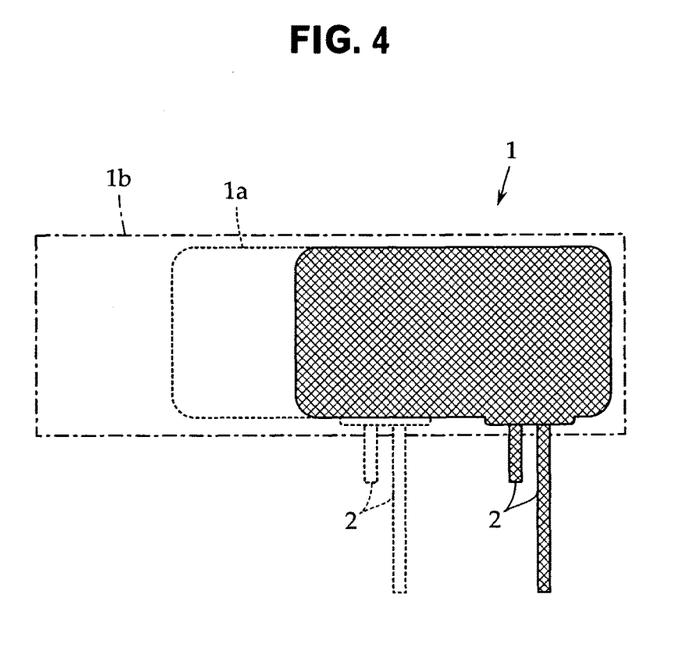
FIG. 4 is a schematic view of a cuff used for a cuff cover in accordance with the present invention.

Prior to the explanation of the cuff cover 10 in accordance with the present invention, the construction of a cuff to which the cuff cover 10 is attached is explained. As shown in FIG. 4, a cuff 1 consists of a pillow-shaped balloon made of rubber, and is integrally provided with two cuff tubes 2 communicating with the interior of the cuff 1.

Of the two cuff tubes 2, one cuff tube 2 is connected with a hand pump, not shown, for feeding air into the cuff 1, and the other cuff tube 2 is connected with a manometer such as a mercury manometer. In FIG. 4, the cuff tubes 2 are arranged on the right-hand side of the cuff 1. However, the cuff tubes 2 are sometimes arranged in the center (the dotted line portion in FIG. 4) of the cuff 1 depending on the type of the cuff 1.

Besides the ordinary size (the hatched portion in FIG. 4) used for the mercury manometer, a large-size cuff 1a (the dotted line portion in FIG. 4) often used for an aneroid manometer or an automatic manometer is also used. Further, an integral cuff 1b (the dash-and-dot line portion in FIG. 4) in which a cover is integrally formed on the cuff 1 is also used. The cuff cover 10 in accordance with the present invention can be applied to all types of cuffs 1, 1a and 1b.

Next, referring to FIGS. 1 and 3, the main cover 20 is formed into a band shape having a length enough to be wound around the upper arm of the human body. In the main cover 20, a first cuff housing portion 21 in which the cuff 1 (refer to FIG. 4) for measuring blood pressure is housed is formed into a bag shape. In this example, the total length of the main cover 20 is 570 mm, and the total width thereof is 150 mm.

In a part of one side (the upper side in FIG. 1) of the main cover 20, a first opening 22 communicating with the first cuff housing portion 21 is provided, and other sides are closed by sewing etc. In this example, the first opening 22 is open so as to have almost the same length (270 mm in this example) as the length in the lengthwise direction (the right and left direction in FIG. 1) of the sub-cover 30 so that the cuff 1 does not move in the main cover 20.

At the other side (the lower side in FIG. 1) of the main cover 20, two first pull-out holes 23 and 24 through which the cuff tubes 2 of the cuff 1 are pulled out are provided. One first pull-out hole 23 is used for the type in which the cuff tubes 2 shown in FIG. 4 are positioned close to the right or left side of the cuff 1. Also, the other first pull-out hole 24 is used for the type in which the cuff tubes 2 are provided in the center of the cuff 1.

In this example, the first pull-out hole 23 is arranged at a position 75 mm distant from the left end of the main cover 20, and the opening width thereof is 25 mm. Also, the second pull-out hole 23 is arranged at a position 170 mm distant from the left end of the main cover 20, and the opening width thereof is 35 mm. Although the opening widths of the first pull-out holes 23 and 24 are different from each other in this example, the opening widths may be equal to each other.

In the present invention, the two first pull-out holes 23 and 24 are provided. However, the positions and the number of first pull-out holes are arbitrary. If the pull-out position of the cuff tubes 2 of the cuff 1 does not coincide with the position of the first pull-out hole 23 or 24, a first pull-out hole may be formed at a desired position by cutting an arbitrary place of the cuff cover 10 using a cutter or the like.

On the tip end side (the right end side in FIG. 1), a reinforcing member 25 is provided to reinforce the end portion of the main cover 20. In this example, the reinforcing member 25 consists of a plat plate shaped wood strip. However, the material and shape of the reinforcing member 25 can be changed arbitrarily according to the specifications.

At the other side (the lower side in FIG. 1) of the main cover 20, a pair of fixing strings 26 and 27 are provided which serve as fixing means for fixing the sub-cover 30 to the main cover 20 in a folded state. The fixing strings 26 and 27 are arranged at positions symmetrical with fixing strings 36 and 37 provided on the sub-cover 30 side.

The main cover 20 is further provided with a pair of surface fasteners 41 and 42 that are used as fixing means for fixing the main cover 20 to the upper arm in a wound state. One surface fastener 41 is arranged in a rectangular form along the width direction on one end side (the right end side in FIG. 1) of the top surface of the main cover 20 as shown in FIG. 1.

The other surface fastener 42 extends in the lengthwise direction from the other end side (the right end side in FIG. 2) to the center of the back surface of the main cover 20 as shown in FIG. 2. In this example, regarding the engagingly attaching surfaces of the surface fasteners 41 and 42, the surface fastener 41 side is a loop surface, and the surface fastener 42 side is a hook surface. However, the engagingly attaching surfaces may be reverse to the above.

As shown in FIG. 1, on the engagingly attaching surface of the surface fastener 41, a first alarm means 43 is provided to indicate that the engagingly attaching state of the cuff cover 10 is shifted in the circumferential direction by the pressure of cuff. The first alarm means 43 is a first alarm line 43 arranged on the inside a predetermined length, 15 mm in this example, distant from the end (the right end in FIG. 1) of the surface fastener 41.

The circumferential direction in the present invention is the circumferential direction of the upper arm of the wearer. In this example, the first alarm line 43 is colored red so as to be discriminated easily.

As shown in FIG. 2, the other surface fastener 42 is provided with a positioning line 44 serving as a positioning means for aligning the center of the cuff 1 with the upper arm artery when the cuff is wound around the upper arm. In this example, the positioning line 44 is colored red so as to be confirmed visually with ease.

The positioning line 44 is provided at a position coinciding relatively with the center position of the cuff 1 in the main cover 20. In this example, the positioning line 44 is arranged at a position 150 mm distant from the right end (refer to FIG. 2) of the main cover 20.

Referring to FIGS. 1 and 3, the sub-cover 30 is formed into a band shape shorter than the main cover 20. In the sub-cover 30, a second cuff housing portion 31 in which the cuff 1 (refer to FIG. 4) for measuring blood pressure is housed is formed into a bag shape.

In this example, the total length of the sub-cover 30 is 270 mm, and the total width thereof is 150 mm. By folding the sub-cover 30 onto the main cover 20, the sub-cover 30 can be lapped on the main cover 30.

In a part of one side (the lower side in FIG. 1) of the sub-cover 30, a second opening 32 communicating with the second cuff housing portion 31 is provided, and other sides are closed by sewing etc.

The sub-cover 30 is provided with a second pull-out hole 33 through which the cuff tubes 2 are pulled out when the cuff 1 is housed in the second housing portion 31. The second pull-out hole 33 is provided on the back surface side (refer to FIG. 2) of the second opening 32 of the sub-cover 30, and is open with an opening width of 40 mm.

In this example, the second pull-out hole 33 is provided only at one place along the second opening 32. However, the second pull-out hole 33 may be provided at two or more places. Further, the second pull-out hole 33 may be provided at the upper side, not at the side on the second opening 32 side.

The sub-cover is provided with second alarm lines 34 and 35 serving as second alarm means that indicate a shift in the axial direction at the time when the cuff 1 is expanded in a state of being wound around the upper arm. The axial direction in the present invention is the lengthwise direction of the upper arm.

As shown in FIG. 2, the second alarm lines 34 and 35 are formed symmetrically in the right and left direction on the inside (6 mm inside the second opening 32 in this example) of the second opening 32 of the sub-cover 30. In this example, the second alarm lines 34 and 35 are colored red so as to be confirmed visually with ease.

The sub-cover 30 is further provided with fixing strings 36 and 37 serving as the other fixing means for fixing the sub-cover 30 to the main cover 20 in a folded state. The fixing strings 36 and 37 are provided at both ends of the upper side of the sub-cover 30.

In this example, the fixing means for fixing the sub-cover 30 to the main cover 20 is formed by the fixing strings 26, 27 (36, 37) to reduce the cost. However, the sub-cover 30 may be fixed to the main cover 20 by a surface fastener or buttons, for example. The method for fixing the sub-cover 30 to the main cover 20 can be changed arbitrarily according to the specifications.

Next, one example of an assembling procedure for housing the cuff 1 (1a, 1b) in the main cover 20 is explained with reference to FIGS. 5A to 5D. In the main cover 20, the large-size cuff 1 (1a, 1b) is housed.

Figure 5A:
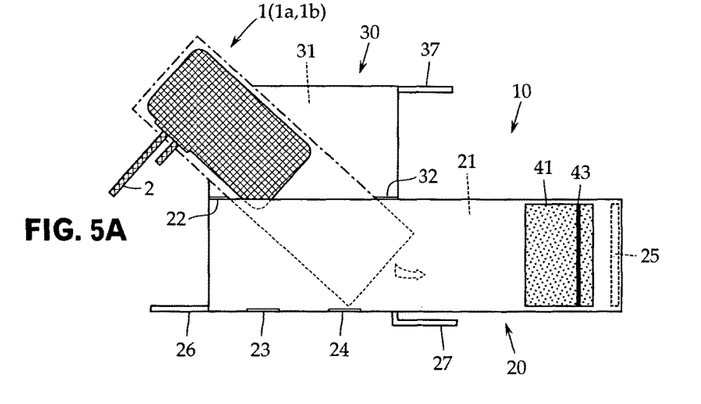
FIGS. 5A to 5D are explanatory views for explaining a procedure for housing a cuff in a main cover.
Figure 5B:
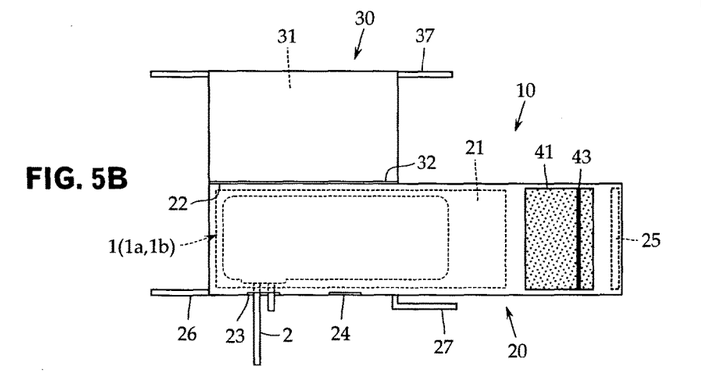
Figure 5C:
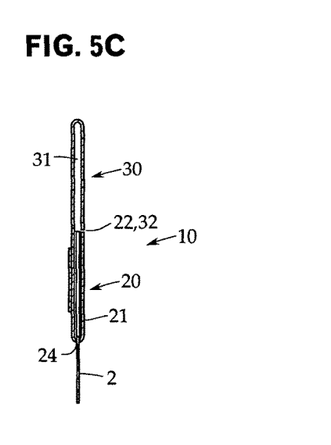

First, as shown in FIG. 5A, the first opening 22 is spread out lightly with fingers etc., and then the cuff 1 (1a, 1b) is inserted little by little through the spread first opening 22 so that the tip end thereof does not bend. Next, as shown in FIGS. 5B and 5C, after the cuff 1 (1a, 1b) has been housed surely in the first cuff housing portion 21, the cuff tubes 2 are pulled out through either of the first pull-out holes 23 and 24. In this example, the first pull-out hole 23 is used.

Figure 5D:
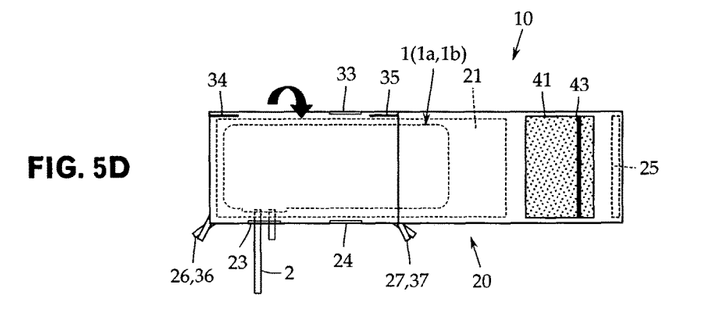

After the cuff 1 (1a, 1b) has been housed in the first cuff housing portion 21, as shown in FIG. 5D, the sub-cover 30 is folded along the main cover 20, and the fixing strings 26 and 36 (27 and 37) are tied up each other to fix the sub-cover 30 to the main cover 20.

At this time, the sub-cover 30 is bent so that the second alarm lines 34 and 35 provided on the sub-cover 30 are on the inside of the main cover 20. By the above-described procedure, the cuff cover 10 is installed, and the cuff is made in a usable state.

Figure 6A:
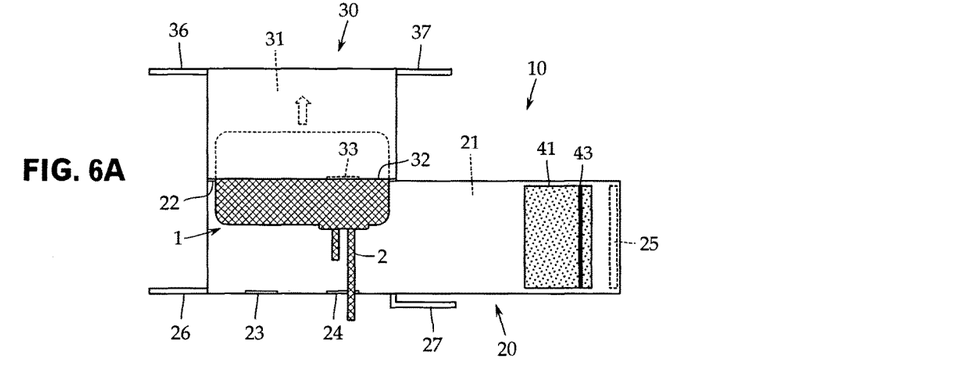
FIGS. 6A to 6D are explanatory views for explaining a procedure for housing a cuff in a sub-cover.

Next, one example of an assembling procedure for housing the cuff 1 (1a, 1b) in the sub-cover 30 is explained with reference to FIGS. 6A to 6D. In the sub-cover 30, the cuff 1 having the ordinary size is housed. First, as shown in FIG. 6A, the second opening 32 is spread out lightly with fingers etc., and then the cuff 1 is inserted through the spread second opening 32.

Figure 6B:
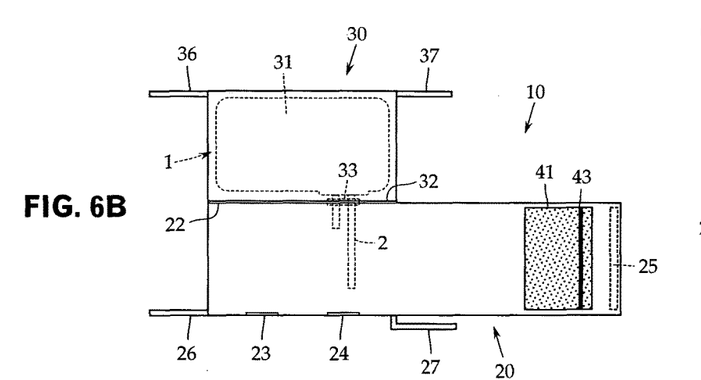
Figure 6C:
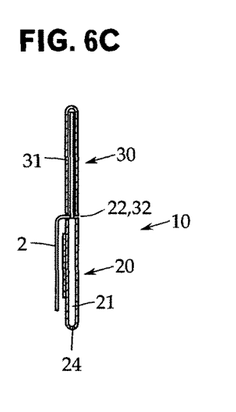

After the cuff 1 has been housed in the second cuff housing portion 31, as shown in FIGS. 6B and 6C, the cuff tubes 2 are pulled out through the second pull-out hole 32. At this time, if the positions of the cuff tubes 2 do not coincide with the existing second pull-out hole 32, a cut may be made at an arbitrary place using a cutter or the like, and the cuff tubes 2 may be pulled out through this cut.

Figure 6D:
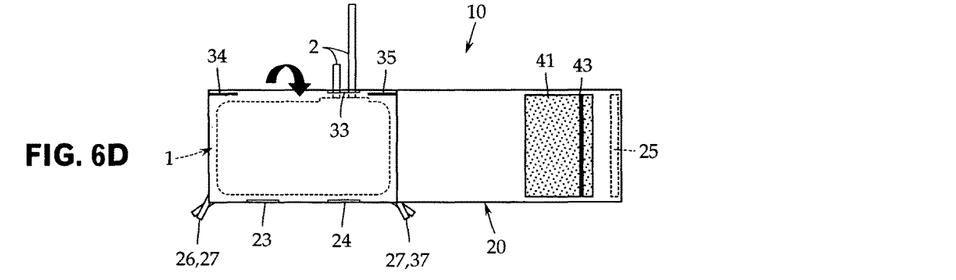

After the cuff tubes 2 have been pulled out, as shown in FIG. 6D, the sub-cover 30 is folded along the main cover 20, and the fixing strings 26 and 36 (27 and 37) are tied up each other to fix the sub-cover 30 to the main cover 20.

At this time, the sub-cover 30 is bent so that the second alarm lines 34 and 35 provided on the sub-cover 30 are on the inside of the main cover 20. By the above-described procedure, the cuff cover 10 is installed, and the cuff is made in a usable state.

Figure 7:
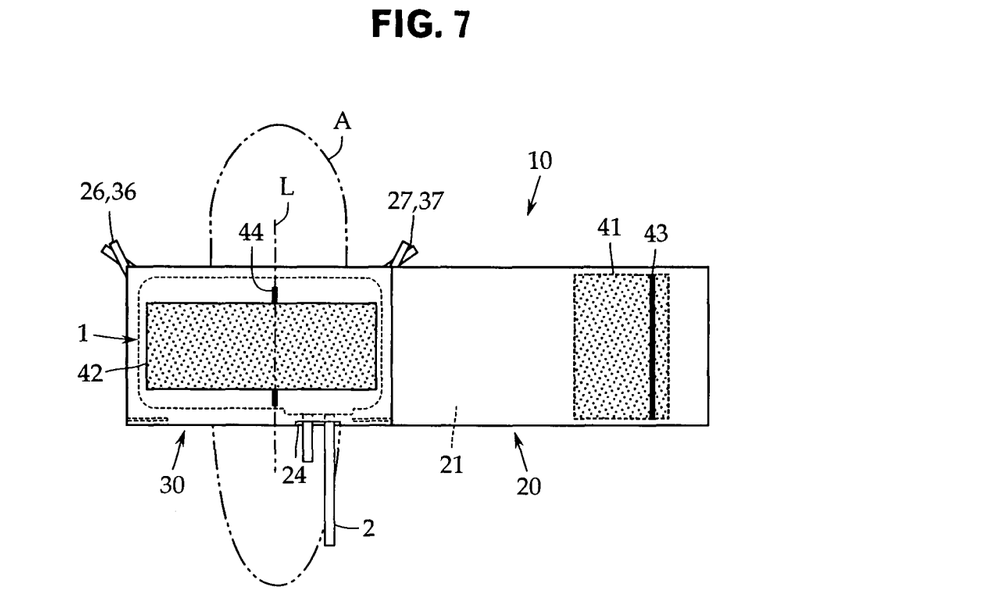
FIG. 7 is an explanatory view for explaining a procedure for using a cuff cover in accordance with the present invention.

In using this cuff, after the hand pump and the manometer, not shown, have been attached to the cuff tubes 2, as shown in FIG. 7, the cuff cover 10 is wound around the upper arm in such a manner that the positioning line 44 of the cuff cover 10 substantially laps on the upper arm artery (the imaginary line L in FIG. 7) of the upper arm A of the human body.

Figure 8:
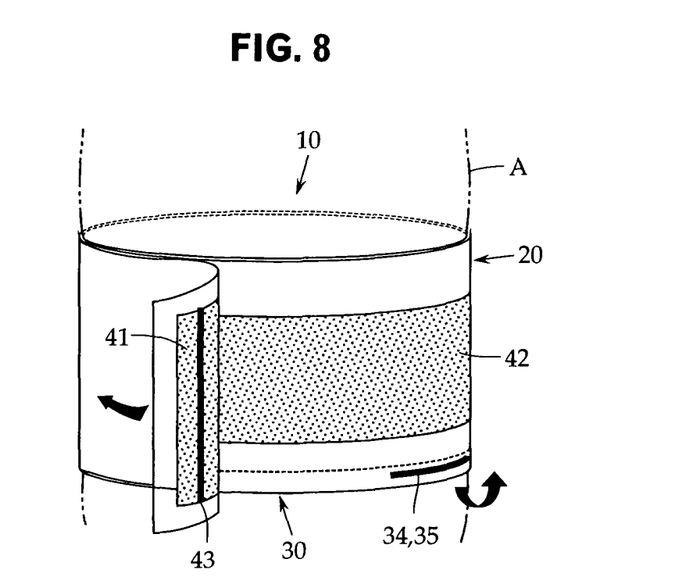
FIG. 8 is an explanatory view for explaining an alarm means of a cuff cover in accordance with the present invention.

Thereby, the upper arm artery is arranged in the center of the cuff 1, and the cuff is mounted on the upper arm. By applying a pressure to the cuff in this state, exact measurement of blood pressure is made. At this time, if the engagingly attaching state of the surface fasteners 42 and 43 is bad, as shown in FIG. 8, the end portion of the main cover 20 gets turned up, and hence the first alarm line 43 provided on the engagingly attaching surface of the surface fastener 41 appears.

In the case where the measurement of blood pressure is continued in the state in which the first alarm line 43 is visible, a proper load is not applied, so that exact measurement of blood pressure cannot be made. Therefore, if the first alarm line 43 is visible, the cuff must be rewound to make the measurement again.

Similarly, if turning-up is produced in the circumferential direction on the sub-cover 30 by the expansion of the cuff 1 when a pressure is applied to the cuff 1, the second alarm lines 34 and 35 on the inside of the sub-cover 30 appear due to the turning-up to the outside. At this time as well, exact measurement of blood pressure cannot be made, so that the cuff must be rewound to make the measurement again.

As described above, for the cuff cover in accordance with the present invention, the conditions of patient can be judged at a glance by using the cuff cover 10 having been color-coded first. Also, the conditions can be written with a pen or the like, so that the cuff cover can be used as triage or a simplified chart.

Also, the cuff cover in accordance with the present invention can contain various cuffs having a different size, and thus can be used without being restricted by the usage place and the facility. Further, even in the case where a shift occurs during the measurement of blood pressure, exact measurement of blood pressure can be made because the cuff cover has the alarm means indicating the shift.

The present application is based on, and claims priority from, Japanese Applications Serial Number JP2006-207883, filed Jul. 31, 2006 the disclosure of which is hereby incorporated by reference herein in its entirety.

The invention claimed is:

1. A cuff cover which houses a cuff for measuring blood pressure therein, comprising:
    a main cover adapted to be wound around an upper arm of a human body and having a first cuff housing portion inside the main cover, wherein the first cuff housing portion is formed in a bag shape having a first opening on one side and is closed on other sides, and
    a sub-cover with a lateral size shorter than that of the main cover, the sub-cover being connected to the main cover along one side thereof to be folded onto the main cover, said sub-cover having a second cuff housing portion inside the sub-cover, wherein the second cuff housing portion is formed in a bag shape separately and independently from the first cuff housing portion, has a second opening on one side, and is closed on other sides,
    wherein the cuff is housed in only one of the first or second cuff housing portions according to a size of the cuff.

2. The cuff cover according to claim 1, wherein the first cuff housing portion is provided with a first tube pull-out hole for pulling out cuff tubes provided on the cuff from the first cuff housing portion.

3. The cuff cover according to claim 2, wherein the first tube pull-out hole is provided at least at two places of the main cover.

4. The cuff cover according to claim 1, wherein the second cuff housing portion is provided with a second tube pull-out hole for pulling out cuff tubes provided on the cuff from the second cuff housing portion.

5. The cuff cover according to claim 1, wherein the main cover and the sub-cover are provided with a fixing device for fixing the covers to each other in a lapped state.

6. The cuff cover according to claim 1, wherein the main cover is provided with a positioning device for aligning a center of the cuff with an upper arm artery when the main cover is wound around the upper arm.

7. The cuff cover according to claim 1, wherein the main cover is provided with a pair of surface fasteners for fixing the main cover in a state of being wound around the upper arm, and on an engagingly attaching surface of the surface fastener, a first alarm device is provided to indicate a shift of an engagingly attaching state in a circumferential direction due to a pressure of the cuff.

8. The cuff cover according to claim 1, wherein the sub-cover is provided with a second alarm device which indicates a shift in an axial direction when the cuff is expanded in a state of being wound around the upper arm.

9. The cuff cover according to claim 1, wherein the cuff cover is provided with a feature describing portion for describing physical conditions and features of a wearer.

10. The cuff cover according to claim 1, wherein the cuff cover is color-coded according to triage or physical conditions, a distinction of sex, and conditions of injuries of a wearer.

11. The cuff cover according to claim 1, wherein each of the main cover and the sub-cover includes an end aligned together, and a side portion connected together, the side portion of the main cover having a first opening for the first cuff housing portion of the main cover at a side of the sub-cover, and the side portion of the sub-cover having a second opening for the second cuff housing portion of the sub-cover at a side of the main cover.

12. The cuff cover according to claim 11, wherein the main cover includes a first tube pull-out hole for pulling out cuff tubes at a side opposite to the first opening, and the sub-cover includes a second tube pull-out hole for pulling out cuff tubes at a side of the second opening.

13. A cuff cover which houses a cuff for measuring blood pressure therein, comprising:
    a main cover adapted to be wound around an upper arm of a human body, and having a first cuff housing portion, wherein the first cuff housing portion is formed in a bag shape having a first opening on one side and is closed on other sides, wherein the first opening communicates with the first cuff housing portion for housing the cuff inside the first cuff housing portion, and
    a sub-cover with a lateral size shorter than that of the main cover, the sub-cover being connected to the main cover along one side thereof to be folded onto the main cover, and having a second cuff housing portion, wherein the second cuff housing portion is formed in a bag shape separately and independently from the first cuff housing portion, has a second opening on one side, and is closed on other sides, and wherein the second opening communicates with the second cuff housing portion for housing the cuff inside the second cuff housing portion,
    wherein the cuff is housed in only one of the first or second cuff housing portion according to a size of the cuff, and the first opening is arranged adjacent to the second opening.

14. The cuff cover according to claim 2, wherein the first tube pull-out hole is provided on one of the closed other sides of the first cuff housing portion.

15. The cuff cover according to claim 1, wherein the second tube pull-out hole is provided on one of the closed other sides of the second cuff housing portion.

* * * * *